United States Patent

Okamoto et al.

[11] Patent Number: 5,977,188
[45] Date of Patent: Nov. 2, 1999

[54] HUMECTANT AND AN ENDERMIC LINIMENT

[75] Inventors: Tohru Okamoto; Reiji Miyahara, both of Yokohama, Japan

[73] Assignee: Shiseido Company, Ltd., Tokyo, Japan

[21] Appl. No.: 09/201,150

[22] Filed: Nov. 30, 1998

[30] Foreign Application Priority Data

Dec. 1, 1997 [JP] Japan ................................. 9-345774

[51] Int. Cl.$^6$ ............................................. A61K 31/045
[52] U.S. Cl. ............................................................ 514/738
[58] Field of Search ............................................. 514/738

[56] References Cited

U.S. PATENT DOCUMENTS

| | | | |
|---|---|---|---|
| 3,993,576 | 11/1976 | Barron | 252/182 |
| 4,521,330 | 6/1985 | Olstowski et al. | 252/51.5 |
| 5,336,501 | 8/1994 | Czech et al. | 424/445 |
| 5,605,681 | 2/1997 | Trandai et al. | 424/65 |
| 5,609,855 | 3/1997 | Oh et al. | 424/65 |

*Primary Examiner*—James H. Reamer
*Attorney, Agent, or Firm*—Townsend & Banta

[57] ABSTRACT

A humectant characteristically comprises a diol represented by the following general formula (I):

$$HO-CH_2-R-CH_2-OH \qquad (I)$$

Wherein R denotes a straight chain or branched chain alkylene group represented by $-(C_nH_{2n})-$ and n denotes an integer 1–3. This a humectant has superior moisture retaining properties and a long lasting skin moisturizing effect, as well as superior usability.

16 Claims, No Drawings

HUMECTANT AND AN ENDERMIC LINIMENT

RELATED APPLICATION

This application claims the priority of Japanese Patent application No.9-345774 filed on Dec. 1, 1997, which is incorporated herein by reference.

BACKGROUND OF THE INVENTION

1. Field of the Invention

This invention relates in general to a humectant and an endermic liniment which contains this humectant, and more particularly to a humectant which has a superior and long lasting skin moisturizing effect and a very good tactile feeling during use (usability), as well as an endermic liniment which contains this humectant.

2. The Prior Art

A normal skin corneum (stratum corneum) usually contains 10–20% of moisture and retains elasticity, flexibility and protective functions. However, when the moisture of the corneum decreases due to changes in the external environment factors such as the temparature and humidity, a condition called dry skin occurs and the skin loses elasticity and protective functions, leading to various troubles.

Conventionally, hydrophilic humectants have been blended into cosmetics for the purpose of improving or preventing such dry skin.

The hydrophilic humectants used for this purpose include the polyol type humectants such as dipropylene glycol, polyglycerine, 1,3-butylene glycol, glycerine, and polyethylene glycol.

However, among these humectants, the triols, the representative example of which is glycerine, have an excellent skin effect on the skin but they have a problem in that their viscosity is so high that blending in enough of them to exhibit the skin moisturizing effect results in stickiness, marring the cosmetic's tactile feeling during use.

On the other hand, 1,3-butylene glycol and dipropylene glycol have little influence on the tactile feeling during use but they have a low skin moisturizing effect and in particular had the problem of their effect being temporary and not long lasting.

A generally used method involves the combined use of glycerine, which has a high moisture retaining capability, and 1,3-butylene glycol and/or dipropylene glycol, which have a good tactile feeling during use. However, it has been known that the moisture retaining action decreases as the glycerine content decreases.

To address the aforementioned problems, the inventors conducted earnest research on the skin moisturizing effect and the molecular structure of polyol for the purpose of achieving an excellent moisture retaining action and an excellent tactile feeling during use at the same time. As a result, the inventors discovered that diol with a specific structure have, in addition to superior usability, a superior skin moisturizing effect and a high rough skin improving action (an excellent skin improving effect on dry and scaly skin) as well as being highly effective in improving small wrinkles on the skin, and also discovered that, by additionally using triol with a specific structure, the moisture retaining action improves even more, the rough skin improving action and the small skin wrinkle improving action improve, and improvement in the tactile feeling during use, a characteristic of triol, is achieved, thus completing the present invention.

BRIEF SUMMARY OF THE INVENTION

The object of the present invention is to provide a humectant which is superior in both its usability and skin moisturizing effect, and also to provide an endermic liniment containing this humectant which is superior in its moisture retaining action, rough skin improving action and small skin wrinkle improving action, and exhibits superior usability.

The present invention provides a humectant characteristically comprising a diol represented by the following general formula (I):

$$HO-CH_2-R-CH_2-OH \qquad (I)$$

wherein R denotes a straight chain or branched chain alkylene group represented by $-(C_nH_{2n})-$ and n denotes an integer 1–3.

Also, the present invention provides said humectant of wherein the diol represented by the general formula (I) is 1,4-butane diol.

Furthermore, the present invention provides said humectant wherein the diol represented by the general formula (I) is 2-methyl-1,3-propane diol.

Also, the present invention provides an endermic liniment characteristically containing a diol represented by the following general formula (I):

$$HO-CH_2-R-CH_2-OH \qquad (I)$$

wherein R denotes a straight chain or branched chain alkylene group represented by $-(C_nH_{2n})-$ and n denotes an integer 1–3.

Furthermore, the present invention provides said endermic liniment wherein the diol represented by the general formula (I) is 1,4-butane diol.

Also, the present invention provides said endermic liniment wherein the diol represented by the general formula (I) is 2-methyl-1,3-propane diol.

Furthermore, the present invention provides said endermic liniment which characteristically contains said diol in the amount of 5–50 wt % of the total endermic liniment.

Also, the present invention provides said endermic liniment which additionally contains a triol which has four or three carbon atoms and three OH groups in the molecule in the amount of 3–20 wt % of the total endermic liniment.

Furthermore, the present invention provides said endermic liniment wherein the sum of said diol content and said triol content is 10–30 wt % of the total endermic liniment and the weight ratio of said diol content and said triol content is 1:3 to 10:1.

DETAILED DESCRIPTION OF THE INVENTION

The configuration of the present invention is described in detail below.

The diol used in the present invention, represented by the aforementioned general formula (I), has the characteristic of both two hydroxyl groups being bonded to primary carbons. Examples include 1,3-propane diol, 2-methyl-1,3-propane diol, 1,4-butane diol and 1,5-pentane diol, among which 1,4-butane diol and 2-methyl-1,3-propane diol are particularly preferable.

The skin moisturinzing effect of polyhydric alcohol is prior art knowledge. The present invention was completed by discovering the fact that the diol with the aforementioned structure, particularly 1,4-butane diol and 2-methyl-1,3-propane diol, exhibit a particularly prominent effect compared with conventional prior art humectants with polyhydric alcohol in terms of their long lasting high skin moisturizing effect and usability.

By using the diol with the aforementioned structure, an endermic liniment with a long lasting high skin moisturizing effect and superior usability can be manufactured. The blend ratio is preferably 5–50 wt %, more preferably 10–20 wt %, of the total amount of the endermic liniment. If it is less than 5 wt %, then the moisture retaining action will not be sufficient. If the blend ratio is 50 wt % or more, no additional improvement in the moisture retaining action is observed and the tactile feeling during use may deteriorate.

When triol with four or three carbon atoms and three OH groups in each of its molecules is blended in addition to the aforementioned essential ingredient in the endermic liniment of the present invention, the skin moisturizing effect and usability will improve. Examples of the triol with four or three carbon atoms and three OH groups in each of its molecules include glycerine, 1,2,3-butane triol and 1,2,4-butane triol.

The blend ratio of the aforementioned triol is 3–20 wt % of the total amount of the endermic liniment. The weight ratio between the aforementioned diol and the aforementioned triol is preferably 1:3 to 10:1, and more preferably 1:2 to 5:1. If the composition ratio of the aforementioned triol component compared with the aforementioned diol component increases, then the stickness of the aforementioned triol component increases and usability deteriorates. If the composition ratio of the aforementioned triol component compared with the aforementioned diol component decreases, then the moisture retaining action decreases and the synergistic effect of mixing these two will be lost.

The endermic liniment of the present invention is a humectant composition and can be manufactured with a conventional method by, according to the target formulation, blending in ingredients which are generally used for ingredients of an endermic liniment including oils, surfactants, humectants other than described above, ultraviolet light absorbents, chelating agents, pH adjustment agents, preservatives, thickeners, pigments, perfume, drugs, etc., in addition to the aforementioned ingredients, within the range which does not affect the effect of the present invention.

The endermic liniment of the present invention can be in any formulation including a solution type, solubilized type, emulsion type, powder dispersion type, water-two phase type and water/oil/powder three phase type. The endermic liniment can be used for any application including liniments for the face, body, scalp or hair on the head such as a toilet water, emulsion, cream, pack and conditioner.

The endermic liniment in the present invention refers to a liniment which is applied on the skin or hair as a cosmetic, drug or quasi-drug.

The present invention can provide a humectant and an endermic liniment which exhibit a high and lasting skin moisturizing effect for alleviation of rough skin, alleviation of small wrinkles on the skin, and improvement in damaged hair, as well as superior tactile feeling during use.

EXAMPLES

Specific descriptions of the present invention are given below by referring to examples. The present invention is not limited to the following examples. The blend ratios are in weight percent units.

The skin moisturizing effect and usability of the humectant and the endermic liniment of the present invention were investigated. That is, based on the recipes in Table 1, the moisture retaining action and usability (tactile feeling during use) were evaluated by using the following testing methods. The results are also shown in Table 1.

Testing Method

For a panel of ten evaluation specialists (n=10), the medial aspect of the forearm was cleaned with a soap and, after 30 minutes in a 23° C. and 50% RH constant temperature and constant humidity chamber, the moisture content in the corneum was measured using a high frequency impedance meter (Skicon 200 from IBS). One microliter/cm$^2$ of the toilet water of the aforementioned Table 1 was applied on the testing site and, after six hours, the toilet water on the skin was removed by cleaning with a soap. The moisture content in the corneum was measured under the same conditions as before the application. The skin moisture retaining action was evaluated by using the corneum moisture content ratio before and after the application.

The moisture retaining actions were evaluated based on the average for n=10 using the following evaluation criteria. A higher value indicates a higher skin moisturizing effect on the skin.

"Evaluation Criteria"

◎: 1.6 or higher
○: 1.3–1.5
Δ: 1–1.2
X: lower than 1

The tactile feeling during use (usability) was evaluated based on the number of people out of n=10 who judged "good" using the following criteria.

"Evaluation Criteria"

◎: Eight or more out of ten reported the tactile feeling during use was good.
○: Six or seven out of ten reported the tactile feeling during use was good.
Δ: Four or five out of ten reported the tactile feeling during use was good.
X: Three or less out of ten reported the tactile feeling during use was good.

TABLE 1

|  | Comparative example 1 | Comparative example 2 | Example 1 | Example 2 | Example 3 | Example 4 | Example 5 | Example 6 |
|---|---|---|---|---|---|---|---|---|
| Dipropylene glycol | 10 | — | — | — | — | — | — | — |
| 1,3-butylene glycol | — | 10 | — | — | — | — | — | — |
| 1,4-butane diol | — | — | 10 | — | 4 | 5 | 20 | 50 |
| 2-methyl-1,3-propane diol | — | — | — | 10 | — | — | — | — |
| Glycerine | — | — | — | — | — | — | — | — |
| Ion exchanged water | 90 | 90 | 90 | 90 | 96 | 96 | 80 | 50 |
| Total | 100 | 100 | 100 | 100 | 100 | 100 | 100 | 100 |
| Moisture retaining action | x | x | ○ | ○ | Δ | ○ | ◎ | ◎ |
| Tactile feeling during use | ○ | ○ | ◎ | ○ | ◎ | ◎ | ○ | Δ |

TABLE 1-continued

|  | Comparative example 3 | Comparative example 4 | Example 7 | Example 8 | Example 9 | Comparative example 5 | Example 10 |
|---|---|---|---|---|---|---|---|
| 1,3-butylene glycol | — | 3 | — | — | — | 15 | — |
| 1,4-butane diol | — | — | 3 | 5 | 10 | — | 15 |
| Glycerine | 10 | 7 | 7 | 5 | 5 | 3 | 3 |
| Ion exchanged water | 90 | 90 | 90 | 90 | 85 | 82 | 82 |
| Total | 100 | 100 | 100 | 100 | 100 | 100 | 100 |
| Moisture retaining action | ⊚ | Δ | ⊚ | ○ | ⊚ | x | ⊚ |
| Tactile feeling during use | x | Δ | ○ | ⊚ | ○ | ○ | ○ |

As clearly shown in Table 1, the diol which is the humectant of the present invention has a superior moisture retaining action compared with 1,3-butylene glycol and/or dipropylene glycol and also exhibits good usability (Example 1 and Comparative examples 1 and 2). As for the diol content of the endermic liniment of the present invention, it was observed that the skin moisturizing effect is low if it is less than 5 wt %, and there was a tendency to have a poorer tactile feeling during use if it is 50 wt % or more (Examples 3–5). As for the cases where glycerine, a triol component, was added, partial substitutions of 1,3-butylene glycol for glycerine revealed that the skin moisturizing effect decreases with less glycerine whereas, when 1,4-butane diol is substituted, the skin moisturizing effect is maintained and the tactile feeling during use, which is characteristically poor when glycerine is used, is improved (Comparative examples 4 and 7).

The rough skin alleviating effect (the skin improving effect) and the small skin wrinkle alleviating effect (the wrinkle improving effect) of the endermic liniment of the present invention were verified by the actual use test. For the actual use test, a panel of 20 female evaluation specialists were divided into two groups and the first group used the toilet waters of Example 11 and Comparative example 6 and the second group used the creams of Example 12 and Comparative example 7; an appropriate amount was applied onto the right and the left halves of the face, respectively, after washing the face twice a day, in the morning and the evening, for two weeks. The rough skin improving effect and the small skin wrinkle improving effect were evaluated based on the numbers of people who reported "effective", "somewhat effective" and "not effective". At the same time, the tactile feeling during use (usability) was evaluated using the same evaluation criteria as in said Example 1. The results are shown in Table 2.

Example 11

Toilet Water

The toilet water was prepared using the following recipe with a conventional method.

| Ethanol | 8 wt % |
|---|---|
| 2-methyl-1,3-propane diol | 5 |
| Glycerine | 5 |
| Polyoxyethylene (20 moles) oleyl alcohol ether | 1.5 |
| Pullulan | 0.05 |
| Jojoba oil | 0.5 |
| Caustic potash | 0.015 |
| EDTA-3Na | 0.01 |
| Preservative | Appropriate amount |
| Perfume | Appropriate amount |
| Ion exchanged water | Balance |

Comparative Example 6

Toilet Water

Preparation was carried out in the same manner as in Example 11.

| Ethanol | 8 wt % |
|---|---|
| Dipropylene glycol | 5 |
| Glycerine | 5 |
| Polyoxyethylene (20 moles) oleyl alcohol ether | 1.5 |
| Pullulan | 0.05 |
| Jojoba oil | 0.5 |
| Caustic potash | 0.015 |
| EDTA-3Na | 0.01 |
| Preservative | Appropriate amount |
| Perfume | Appropriate amount |
| Ion exchanged water | Balance |

Example 12

Cream

The cream was prepared using the following recipe with a conventional method.

| Polyethylene glycol 4000 | 1 wt % |
|---|---|
| 1,4-butane diol | 5 |
| 2-methyl-1,3-propane diol | 5 |
| Glycerine | 5 |
| Squalane | 20 |
| Vaseline | 5 |
| Cetostearyl alcohol | 3 |
| Polyoxyethylene (20 moles) oleyl alcohol ether | 1.5 |
| Glyceryl monostearate | 1.5 |
| Urea | 2 |
| Sodium lactate | 1 |
| Xanthan gum | 0.05 |
| Preservative | Appropriate amount |
| Caustic potash | 0.01 |
| EDTA-3Na | 0.01 |
| Preservative | Appropriate amount |
| Ion exchanged water | Balance |

Comparative Example 7

Cream

Preparation was carried out in the same manner as in Example 12.

| | |
|---|---|
| Polyethylene glycol 4000 | 1 wt % |
| 1,3-butylene glycol | 10 |
| Glycerine | 5 |
| Squalane | 20 |
| Vaseline | 5 |
| Cetostearyl alcohol | 3 |
| Polyoxyethylene (20 moles) oleyl alcohol ether | 1.5 |
| Glyceryl monostearate | 1.5 |
| Urea | 2 |
| Sodium lactate | 1 |
| Xanthan gum | 0.05 |
| Preservative | Appropriate amount |
| Caustic potash | 0.01 |
| EDTA-3Na | 0.01 |
| Preservative | Appropriate amount |
| Ion exchanged water | Balance |

TABLE 2

| | Example 11 | Comparative example 6 | Example 12 | Comparative example 7 |
|---|---|---|---|---|
| "Rough skin improving effect" | | | | |
| Effective | 5 | 2 | 7 | 3 |
| Somewhat effective | 4 | 3 | 3 | 3 |
| Not effective | 1 | 5 | 0 | 4 |
| Efficacy ratio | 90% | 50% | 100% | 60% |
| "Small skin wrinkle improving effect" | | | | |
| Effective | 2 | 1 | 4 | 2 |
| Somewhat effective | 3 | 2 | 4 | 2 |
| Not effective | 5 | 7 | 2 | 6 |
| Efficacy ratio | 60% | 30% | 80% | 40% |
| "Tactile feeling during use" | ⊚ | ○ | ⊚ | ○ |

As clearly shown in Table 2, the endermic liniment of the present invention was superior in terms of its rough skin improving effect and small skin wrinkle improving effect, and also exhibited good usability.

Other examples of the endermic liniment of the present invention are shown below.

Example 13

Emulsion

The emulsion was prepared using the following recipe with a conventional method.

| | |
|---|---|
| 2-methyl 1,3-propane diol | 7 |
| Glycerine | 5 |
| Sodium pyrrolidonecarboxylate | 0.5 |
| Squalane | 5 |
| Vaseline | 1 |
| Cetostearyl alcohol | 0.3 |
| Polyoxyethylene (20 moles) oleyl alcohol ether | 1.5 |
| Sodium polyacrylate | 0.03 |
| Preservative | 0.2 |
| Caustic potash | 0.1 |
| EDTA-3Na | 0.03 |
| Perfume | Appropriate amount |
| Ion exchanged water | Balance |

Comparative Example 8

Emulsion

Preparation was carried out in the same manner as in Example 13.

| | |
|---|---|
| 1,3-butylene glycol | 7 |
| Glycerine | 5 |
| Sodium pyrrolidonecarboxylate | 0.5 |
| Squalane | 5 |
| Vaseline | 1 |
| Cetostearyl alcohol | 0.3 |
| Polyoxyethylene (20 moles) oleyl alcohol ether | 1.5 |
| Sodium polyacrylate | 0.03 |
| Preservative | 0.2 |
| Caustic potash | 0.1 |
| EDTA-3Na | 0.03 |
| Perfume | Appropriate amount |
| Ion exchanged water | Balance |

Example 14

Cream

The cream was prepared using the following recipe with a conventional method.

| | |
|---|---|
| 1,4-butane diol | 15 wt % |
| Glycerine | 3 |
| Erythritol | 1 |
| Cetostearyl alcohol | 4 |
| Vaseline | 5 |
| Squalane | 3 |
| Jojoba oil | 3 |
| Dimethyl silicone (6 mPa · s) | 5 |
| Glyceryl monostearate | 2.5 |
| Polyoxyethylene (5 moles) glyceryl monostearate | 1.5 |
| Polyoxyethylene (20 moles) oleyl alcohol ether | 3 |
| Vitamin E acetate | 0.05 |
| Preservative | Appropriate amount |
| EDTA-3Na | 0.03 |
| Perfume | Appropriate amount |
| Ion exchanged water | Balance |

Comparative Example 9

Cream

Preparation was carried out in the same manner as in Example 14.

| | |
|---|---|
| Dipropylene glycol | 15 wt % |
| Glycerine | 3 |
| Erythritol | 1 |
| Cetostearyl alcohol | 4 |
| Vaseline | 5 |

-continued

| | |
|---|---|
| Squalane | 3 |
| Jojoba oil | 3 |
| Dimethyl silicone (6 mPa · s) | 5 |
| Glyceryl monostearate | 2.5 |
| Polyoxyethylene (5 moles) glyceryl monostearate | 1.5 |
| Polyoxyethylene (20 moles) oleyl alcohol ether | 3 |
| Vitamin E acetate | 0.05 |
| Preservative | Appropriate amount |
| EDTA-3Na | 0.03 |
| Perfume | Appropriate amount |
| Ion exchanged water | Balance |

Example 15

Hair Treatment

The hair treatment was prepared using the following recipe with a conventional method.

| | |
|---|---|
| 1,4-butane diol | 10 wt % |
| Cetostearyl alcohol | 3 |
| Stearyltrimethylammonium chloride | 2 |
| Dimethyl silicone (20 mPa · s) | 10 |
| Preservative | Appropriate amount |
| Perfume | Appropriate amount |
| Ion exchanged water | Balance |

Comparative Example 10

Hair Treatment

Preparation was carried out in the same manner as in Example 15.

| | |
|---|---|
| 1,3-butane diol | 10 wt % |
| Cetostearyl alcohol | 3 |
| Stearyltrimethylammonium chloride | 2 |
| Dimethyl silicone (20 mPa · s) | 10 |
| Preservative | Appropriate amount |
| Perfume | Appropriate amount |
| Ion exchanged water | Balance |

Compared with Comparative example 10, the hair treatment of Example 15 had an improved moisture retaining action and superior usability.

What is claimed is:

1. A humectant comprising from 5–20 wt % of a diol represented by the following formula (I):

$$HO-CH_2-R-CH_2-OH \quad (I)$$

wherein R denotes a straight chain or branched chain alkylene group represented by $-(C_nH_{2n})-$, and n denotes an integer 1–3.

2. The humectant of claim 1, wherein the diol represented by the formula (I) is 1,4-butane diol.

3. The humectant of claim 1, wherein the diol represented by the formula (I) is 2-methyl-1,3-propane diol.

4. An endermic liniment containing from 5–20 wt % of a diol represented by the following formula (I):

$$HO-CH_2-R-CH_2-OH \quad (I)$$

wherein R denotes a straight chain or branched chain alkylene group represented by $-(C_nH_{2n})-$, and n denotes an integer 1–3.

5. The endermic liniment of claim 4, wherein the diol represented by the formula (I) is 1,4-butane diol.

6. The endermic liniment of claim 4, wherein the diol represented by the formula (I) is 2-methyl-1,3-propane diol.

7. The endermic liniment of claim 4, which additionally contains a triol having three or four carbon atoms and three OH groups in the molecule, said triol being present in an amount of from 3–20 wt % of the total endermic liniment.

8. The endermic liniment of claim 7, wherein the sum of the diol and triol contents is from 10–30 wt % of the total endermic liniment, and the weight ratio of the diol and triol contents is from 1:3 to 10:1.

9. A method for alleviating rough skin and small skin wrinkles comprising applying to the skin a endermic liniment comprising from 5–20 wt % of a diol represented by formula (I):

$$HO-CH_2-R-CH_2-OH \quad (I)$$

wherein R denotes a straight chain or branched chain alkylene group represented by $-(C_nH_{2n})-$, and n denotes an integer 1–3.

10. The method of claim 9, wherein the diol represented by the formula (I) is 1,4-butane diol.

11. The method of claim 9, wherein the diol represented by the formula (I) is 2-methyl-1,3-propane diol.

12. The method of claim 10, wherein the endermic liniment additionally contains a triol having three or four carbon atoms and three OH groups molecule, said triol being present in an amount of from 3–20 wt % of the total endermic liniment.

13. The method of claim 12, wherein the sum of the diol and triol contents is from 10–30 wt % of the total endermic liniment, and the weight ratio of the diol and triol contents is from 1:3 to 10:1.

14. The method of claim 9, wherein the endermic liniment is a toilet water.

15. The method of claim 9, wherein the endermic liniment is a cream.

16. The method of claim 9, wherein the endermic liniment is in the form of an emulsion.

* * * * *